US009046471B2

(12) United States Patent
Ueji (10) Patent No.: US 9,046,471 B2
(45) Date of Patent: Jun. 2, 2015

(54) X-RAY MEASUREMENT APPARATUS (71) Applicant: RIGAKU CORPORATION, Akishima-shi (JP)

(72) Inventor: Yoshinori Ueji, Akishima (JP)

(73) Assignee: RIGAKU CORPORATION, Tokyo (JP)

( * ) Notice: Subject to any disclaimer, the term of this patent is extended or adjusted under 35 U.S.C. 154(b) by 101 days.

(21) Appl. No.: 13/757,187

(22) Filed: Feb. 1, 2013

(65) Prior Publication Data

US 2013/0259199 A1    Oct. 3, 2013

(30) Foreign Application Priority Data

Mar. 27, 2012  (JP) ................. 2012-072559

(51) Int. Cl.
  *A61B 6/00*    (2006.01)
  *G06T 11/00*   (2006.01)
  *G01N 23/20*   (2006.01)

(52) U.S. Cl.
  CPC ............. *G01N 23/20008* (2013.01); *A61B 6/58* (2013.01); *A61B 6/547* (2013.01); *A61B 6/586* (2013.01); *A61B 6/587* (2013.01); *A61B 6/5264* (2013.01); *G06T 11/005* (2013.01)

(58) Field of Classification Search
  CPC .. A61B 6/5258; A61B 6/5264; A61B 6/5294; A61B 6/547; A61B 6/58; A61B 6/586; A61B 6/587; G06T 11/005
  USPC ............. 378/70–78, 82–85, 86–90, 193, 197, 378/198, 204, 207, 210; 250/200, 201, 250/201.2, 206, 206.1, 206.2, 557, 215, 21, 250/227.2, 239, 491.1, 522.1, 526
  See application file for complete search history.

(56) References Cited

U.S. PATENT DOCUMENTS

| 7,377,172 | B2 * | 5/2008 | Jensen et al. ................ 73/702 |
| 7,581,885 | B2 * | 9/2009 | Ertel et al. ................ 378/206 |
| 2003/0048877 | A1 * | 3/2003 | Price et al. ................ 378/203 |
| 2004/0022355 | A1 * | 2/2004 | Kaiser et al. ................ 378/49 |
| 2006/0039530 | A1 * | 2/2006 | Kenning et al. ................ 378/44 |
| 2007/0075250 | A1 * | 4/2007 | Malmin ................ 250/363.08 |
| 2009/0274274 | A1 | 11/2009 | He et al. |
| 2012/0051507 | A1 | 3/2012 | Hasegawa et al. |

FOREIGN PATENT DOCUMENTS

| JP | 2007163262 A | 6/2007 |
| JP | 2012052817 A | 3/2012 |

* cited by examiner

*Primary Examiner* — Anastasia Midkiff
(74) *Attorney, Agent, or Firm* — Buchanan Ingersoll & Rooney PC (57) ABSTRACT

A portable, for example, a hand-held-type, X-ray measurement apparatus, wherein the vibration or hand-shaking of the X-ray measurement apparatus is detected by a vibration-detection sensor such as a distance sensor, a gyro sensor, or the like, and a measurement value for the X-ray intensity obtained using a two-dimensional X-ray detector is corrected on the basis of a variation quantity obtained using the vibration-detection sensor. The correction may be a correction related to an X-ray source, a correction related to an X-ray detector, a correction calculated using the CPU of a computer and a software program, or the like.

19 Claims, 4 Drawing Sheets

| MEASUREMENT | INCIDENT ANGLE | | RADIATION POSITION ON MEASUREMENT OBJECT | | | DETECTOR POSITION | | SINGLE-SHOT | INTEGRATED |
|---|---|---|---|---|---|---|---|---|---|
| | θi (°) | Φi (°) | Xs | Ys | Zs | θd (°) | Rd (°) | | |
| 1 | 20 | 0 | 0 | 0 | 0 | 20 | 100 | (a) | (a) |
| 2 | 21 | 0 | 0 | 0 | 10 | 21 | 105 | (b) | |
| 3 | 19 | 1 | 1 | 0 | 1 | 21 | 100 | (c) | (a+c) |
| 4 | 20 | 0 | 0 | 2 | 0 | 20 | 98 | (d) | (a+c+d) |

X-RAY MEASUREMENT APPARATUS

BACKGROUND OF THE INVENTION

1. Field of the Invention

The present invention relates to an X-ray measurement apparatus in which an X-ray source and an X-ray detection means are accommodated in a portable housing.

2. Description of the Related Art

Conventionally, a portable X-ray measurement apparatus is disclosed, for example, in Patent Document 1. In the X-ray measurement apparatus, an X-ray source and an X-ray detection means are stored within a housing. The X-ray measurement apparatus can be brought into various measuring positions to perform X-ray measurement, making the apparatus extremely useful.

This type of portable X-ray measurement apparatus may move due to vibration of the apparatus itself or hand-shaking during measurement. In particular, when the portable X-ray measurement apparatus is a hand-held type of X-ray measurement apparatus, the effect of hand-shaking may be high, preventing the acquisition of accurate data.

In the case of the X-ray measurement apparatus disclosed in Patent Document 1, the portion around the X-ray opening for outputting an X-ray and capturing the diffracted X-ray that has left the measurement object is pressed against the measurement object via a rubber ring member, whereby the occurrence of hand-shaking or position variation in the X-ray measurement apparatus is avoided.

However, radiating an X-ray at a fixed position on the measurement object during measurement, and detecting the diffracted X-ray from the measurement object with the X-ray detector at a stable, correct diffraction angle with no variation are required conditions for obtaining highly reliable measurement data with an X-ray measurement apparatus, and it is not possible to adequately fulfill those requirements by holding the X-ray measurement apparatus using only a rubber ring member.

Prior Art Literature (Patent Citation 1): US Patent Application Publication US 2009/0274274

SUMMARY OF THE INVENTION

The present invention was developed in view of the problems of a conventional apparatus described above, and an object of the present invention is to provide an X-ray measurement apparatus capable of obtaining correct, stable, highly reliable measurement data despite the fact that the X-ray measurement apparatus is portable, and is therefore vulnerable to being affected by hand-shaking, vibration, and the like during measurement.

The X-ray measurement apparatus according to the present invention has an X-ray source for generating an X-ray that is incident on a measurement object, an X-ray detection means for detecting an X-ray leaving the measurement object, and a housing for accommodating the X-ray source and the X-ray detection means, wherein the X-ray measurement apparatus further has a vibration quantity detection sensor for detecting the vibration quantity of the housing, and a process for correcting a measurement value obtained using the X-ray detection means is performed on the basis of the vibration quantity obtained using the vibration quantity detection sensor.

The X-ray leaving the measurement object may be, for example, an X-ray diffracted by the measurement object, an X-ray scattered by the measurement object, an X-ray emerging from the measurement object, or an X-ray emitted from the measurement object.

In the X-ray measurement apparatus thus configured, the housing is a portable housing, or a housing capable of being carried by a person (in other words, is a hand-held type). When an X-ray measurement apparatus is formed as a portable or hand-held type in this manner, it is more vulnerable to being affected by vibration than a fixed-type X-ray measurement apparatus, but when the present invention is applied, the effect of vibration can be effectively relieved.

According to the X-ray measurement apparatus thus configured, vibration is detected and a measurement value is corrected on the basis of the detection results. Therefore, correct, stable, highly reliable measurement data can be obtained despite the fact that the X-ray measurement apparatus is portable, and is therefore vulnerable to being affected by hand-shaking, vibration, and the like during measurement.

Examples of processes for correcting a measurement value obtained by the X-ray detection means in the configuration described above include the following:

(A) software correction of the measurement value determined by the X-ray detection means, the correction being performed by an appropriate software application;

(B) adjustment of the position of the X-ray source and/or the X-ray optical element OE1 (see FIG. 1. for example) constituting the optical system on the incident side of the X-ray measurement apparatus to adjust the X-ray radiated toward the measurement object; and (C) adjustment of the position of the X-ray detection means and/or the X-ray optical element OE2 (see FIG. 1. for example) constituting the optical system on the light-receiving side of the X-ray measurement apparatus to adjust the state of the X-ray for the X-ray capture area of the X-ray detection means.

The X-ray measurement apparatus according to the present invention detects vibration of the housing or hand-shaking in the hand that holds the housing, and corrects the measurement value on the basis of the detection results. Therefore, correct, stable, highly reliable measurement data can be obtained despite the fact that the X-ray measurement apparatus is portable, and is therefore vulnerable to being affected by hand-shaking, vibration, and the like during measurement.

The vibration quantity detection sensor in the X-ray measurement apparatus according to the present invention is capable of detecting at least one of the following:

(A) the amount of variation in distance between the vibration quantity detection sensor and the measurement object;

(B) the amount of variation within a plane orthogonal to a line connecting the vibration quantity detection sensor and the measurement object; and (C) the amount of variation in inclination of the vibration quantity detection sensor relative to the measurement object.

The vibration quantity detection sensor in the X-ray measurement apparatus according to the present invention can be one or a combination of two or more of a distance sensor for detecting variation in distance, a speed sensor for detecting variation in speed, an acceleration sensor for detecting variation in acceleration, and an angular velocity sensor for detecting variation in angular velocity.

The distance sensor can, for example, be a sensor for measuring distance on the basis of the time from emission of the laser light to reception of the light. The angular velocity sensor can, for example, be a gyro sensor.

For example, it is possible to determine change data on the amount of change such as vibration, hand-shaking, or the like by performing calculation on the basis of speed data obtained by the speed sensor, to generate a command signal for correcting the vibration and the like on the basis of the data on the amount of change, and to correct the vibration of the X-ray measurement apparatus on the basis of the correction command signal. It is also possible, for example, to perform a Fourier transform on the speed data obtained by the acceleration sensor to determine the vibration speed data and vibration quantity data.

It is also possible, for example, to obtain angular velocity data using the gyro sensor and movement direction data using the acceleration sensor to determine the inclination angle of the X-ray measurement apparatus on the basis of the data obtained. It is also possible, for example, to obtain angular velocity data using the gyro sensor and integrate the angular velocity data to obtain the change in angle of the X-ray measurement apparatus.

The vibration quantity detection sensor in the X-ray measurement apparatus according to the present invention can be secured to the housing. The securing position may be inside or outside the housing. If the vibration quantity detection sensor is secured to the housing, the sensor can accurately detect the quantity of vibration of the housing.

The process for correcting a measurement value obtained using the X-ray detection means in the X-ray measurement apparatus according to the present invention can be a process for controlling the position of the X-ray detection means. The position of the X-ray detection means can, for example, be controlled using a device, for example, an actuator, for mechanically moving the X-ray detection means. Further, the apparatus for controlling the action of the actuator can be constituted by a combination of, for example, the central processing unit (CPU) of a computer and a software program.

The process for controlling the position of the X-ray detection means in the X-ray measurement apparatus according to the present invention can cause variation in the distance between the X-ray detection means and the measurement object. By doing this, it is possible to correct the intensity of the X-ray measured by the X-ray detection means.

The process for controlling the position of the X-ray detection means in the X-ray measurement apparatus according to the present invention can cause movement of the X-ray detection means in a direction at a right angle to the center line of the X-ray leaving the measurement object. By doing this, it is possible to correct the X-ray detection angle measured by the X-ray detection means.

The process for controlling the position of the X-ray detection means in the X-ray measurement apparatus according to the present invention can be a process for causing variation in the inclination angle of the X-ray detection means in relation to the measurement object. By doing this, it is possible to correct the angle and intensity at which the X-ray is captured in the X-ray capture unit region.

The process for controlling the position of the X-ray detection means in the X-ray measurement apparatus according to the present invention can be a combination of two or three of the following:
 (A) causing variation in the distance between the X-ray detection means and the measurement object;
 (B) causing movement of the X-ray detection means in a direction at a right angle to the center line of the X-ray emitted from the measurement object; and
 (C) causing variation in the inclination angle of the X-ray detection means in relation to the measurement object.

The process for correcting a measurement value obtained using the X-ray detection means in the X-ray measurement apparatus according to the present invention can be a process for causing the X-ray that leaves the X-ray source and incident on the measurement object to be incident on the measurement object at a fixed position.

The X-ray that leaves the X-ray source may be, for example, the X-ray that is emitted from the X-ray source or the X-ray that emerges from the X-ray source.

This type of process can be performed, for example, by controlling the orientation of the X-ray source in relation to the measurement object, by controlling the direction of advance of the X-ray leaving the X-ray source by controlling the position of at least one of a plurality of X-ray optical elements constituting the incident optical system, or the like. The X-ray optical elements may be an X-ray tube, a monochromator, a slit, or the like.

The apparatus for controlling the orientation of the X-ray source, the position of the X-ray optical elements, or the like may, for example, be an apparatus for mechanically or electrically moving the X-ray source, such as an actuator; or an apparatus for varying the direction of advance of the X-ray leaving the X-ray source using a magnetic field; or the like. The apparatus for controlling the action of an actuator or the like can also be constituted by a combination of, for example, the central processing unit (CPU) of a computer and a software program.

The process for correcting a measurement value obtained using the X-ray detection means in the X-ray measurement apparatus according to the present invention can be a process in which the data obtained by the X-ray detection means is processed using calculations produced by a software program. An apparatus for performing this type of process can be constituted by a combination of, for example, the central processing unit (CPU) of a computer and a software program.

The X-ray detection means in the X-ray measurement apparatus according to the present invention can be any of a one-dimensional X-ray detector, a two-dimensional X-ray detector, or a pixel detector. A one-dimensional X-ray detector is an X-ray detector having positional resolution for X-ray intensity in a linear direction. A one-dimensional X-ray detector can be formed with, for example, a plurality of minute X-ray light-receiving elements capable of detecting an X-ray and lined up in a straight line.

A two-dimensional X-ray detector is an X-ray detector having positional resolution for X-ray intensity in a plane. A two-dimensional X-ray detection means can be formed with, for example, a semiconductor X-ray detector formed by lining up a plurality of minute X-ray light-receiving elements in a plane. A two-dimensional X-ray detection means can be formed using a detector with a configuration allowing detection of an X-ray for each pixel and output of a signal for each pixel. For example, the two-dimensional X-ray detection means can be configured using a semiconductor image sensor formed by lining up a plurality of semiconductor X-ray light-receiving elements in a plane. For this type of semiconductor X-ray light-receiving element, a charge-coupled device (CCD) or a complementary metal-oxide semiconductor (CMOS), for example, may be used.

The two-dimensional X-ray detection means may also be configured with a photon-counting-pixel two-dimensional X-ray detector, namely, a pulse-counting-pixel-array two-dimensional detector. A photon-counting-pixel two-dimensional X-ray detector is an X-ray detector formed by aligning in two dimensions a plurality of pixels (picture elements) in which photons excited by an X-ray are directly converted to electrical signals.

The housing of the X-ray measurement apparatus according to the present invention can be configured so as to allow a person to carry the housing by hand. It is then possible for the person to perform measurement while manually holding the housing and placing the opening in the housing for outputting an X-ray so that the opening faces the measurement object.

DESCRIPTION OF THE PREFERRED EMBODIMENTS

Following, the X-ray measurement apparatus according to the present invention is explained on the basis of the embodiments. The present invention is of course not limited to the above-described embodiments, and in order to show the characteristic portions of the invention in a manner that is easy to understand, in some cases the constituent elements of the invention are shown in the drawings attached to this specification in proportions differing from the actual object.

(First Embodiment)

Figure 1:
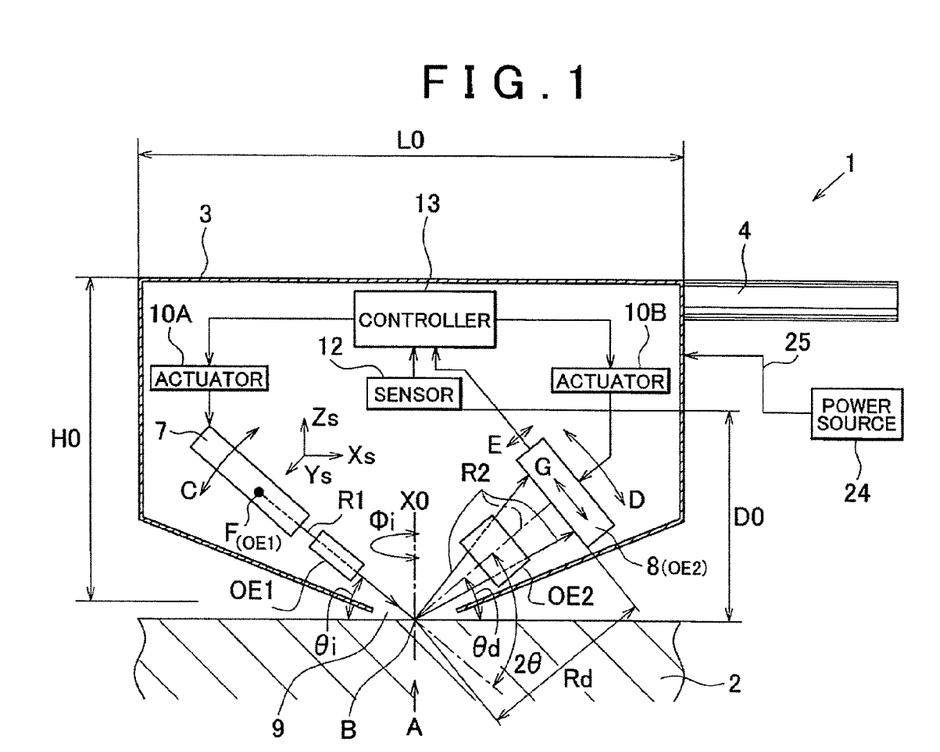
FIG. 1 is a lateral sectional view of an embodiment of the X-ray measurement apparatus according to the present invention.

FIG. 1 shows an embodiment of the X-ray measurement apparatus according to the present invention. In the embodiment, An X-ray measurement apparatus 1 is an apparatus for non-destructively examining whether a defect exists in a measurement object 2 using an X-ray. The X-ray measurement apparatus in this embodiment is a so-called hand-held-type X-ray measurement apparatus. It is clear that the present invention can also be applied to a portable X-ray measurement apparatus that is a type other than a hand-held type.

The X-ray measurement apparatus 1 has a housing formed with an X-ray-impermeable material, namely, a container 3. The X-ray-impermeable material is a material containing at least one of, for example, iron, tungsten, or molybdenum. A handle 4 is secured to one part of the external peripheral surface of the container 3. The handle 4 is formed in a pillar shape such as a round columnar or rectangle columnar shape or the like, extending toward the outer-side direction (namely, the lateral direction in FIG. 1) of the housing 3. The handle 4 is a size allowing the person performing the measurement to grasp the handle with one or both hands. Ideally, a surface treatment designed to make the surface of the handle 4 non-slipping is applied to the handle 4.

The size of the housing 3 is set, for example, to a length L0 of 100 mm to 300 mm; a width of 100 mm to 250 mm, the width being the length in the direction orthogonal to the length L0 (namely, the direction passing through the surface of the drawing); and a height H0 of 75 mm to 200 mm.

The interior of the housing 3 accommodates an X-ray tube 7 that is an X-ray generating device, and a two-dimensional X-ray detector 8 that is an X-ray detection means. The interior of the X-ray tube 7 accommodates, for example, a filament which is a cathode (not shown) and a target which is an anticathode (not shown). The filament generates heat with electric current to emit thermal electrons. The region where the emitted thermal electrons collide with the target is an X-ray focus F, and an X-ray is generated from the X-ray focus F. The X-ray generated in this manner is emitted outside the X-ray tube 7, as shown schematically by arrow R1.

The X-ray emitted from the X-ray tube 7 and radiated at the measurement object 2 is, depending on the type of measurement, a continuous X-ray or a monochromatic X-ray. A monochromator, a filter, or the like is installed in the X-ray light path when a monochromatic X-ray is used. The X-ray measurement apparatus 1 in this embodiment may be an apparatus for performing measurement on the basis of a focusing method, an apparatus for performing measurement on the basis of a parallel beam method, or a fluorescent X-ray measurement apparatus.

When measurement is performed on the basis of the focusing method, the X-ray generated and divergent from the X-ray source F is incident on the measurement object 2, and the X-ray diffracted by the measurement object 2 is focused at one point on the light-receiving surface of the X-ray detector 8. When measurement is performed on the basis of the parallel beam method, the X-ray optical element (for example, a collimator, a Soller slit, or the like) for collimating a divergent X-ray beam is placed on the incident side and/or on the light-receiving side. When fluorescent X-ray measurement is performed, a dispersive crystal for selecting an X-ray by wavelength and extracting the X-ray is placed on the light-receiving side.

An aperture 9 for emitting to the outside of the housing 3 the X-ray emitted from the X-ray tube 7 is provided to the bottom surface of the housing 3. The aperture 9 is in the shape of a circle or a rectangular, or a shape close to one of those, as viewed from the direction of arrow A. During measurement, the housing 3 is placed relative to the measurement object 2 so that the aperture 9 is facing the measurement object 2. An X-ray passing through the aperture 9 is thus radiated at the surface of the measurement object 2.

The two-dimensional X-ray detector 8 in this embodiment is formed with a semiconductor X-ray detector formed by aligning a plurality of minute X-ray light-receiving elements within a plane. The two-dimensional X-ray detector 8 is a detector with a configuration allowing detection of an X-ray for each pixel and output of a signal for each pixel. For example, the two-dimensional X-ray detector 8 can be configured using a semiconductor image sensor formed by aligning a plurality of semiconductor X-ray light-receiving elements within a plane. For this type of semiconductor X-ray light-receiving element, a charge-coupled device (CCD) or a complementary metal-oxide semiconductor (CMOS), for example, may be used.

The two-dimensional X-ray detector 8 may also be configured using a photon-counting-pixel two-dimensional X-ray detector, namely, a pulse-counting-pixel-array two-dimensional detector. A photon-counting-pixel two-dimensional X-ray detector is an X-ray detector formed by aligning in two dimensions a plurality of pixels (picture elements) in which photons excited by an X-ray are directly converted to electrical signals.

In place of the two-dimensional X-ray detector 8, a one-dimensional X-ray detector may also be used. A one-dimensional X-ray detector can be configured using, for example, a semiconductor image sensor formed by aligning a plurality of semiconductor X-ray light-receiving elements within a plane. For this type of semiconductor X-ray light-receiving element, a charge-coupled device (CCD) or a complementary metal-oxide semiconductor (CMOS), for example, may be used.

Inside the housing 3 in FIG. 1, a vibration quantity detection sensor 12 and a controller 13 are installed. The vibration quantity detection sensor 12 has sensors such as a distance sensor for detecting distance using laser light, a speed sensor for detecting variation in speed, an acceleration sensor for detecting acceleration, and a gyro sensor functioning as an angular velocity sensor for detecting angular velocity. One, two, or three of the sensors may be used in combination as needed.

An actuator 10A is coupled with the X-ray tube 7. The actuator 10A can perform the following actions:
(1) To adjust the position of the X-ray tube 7, the actuator can cause the X-ray tube to rotatably oscillate around the X-ray radiation point B as shown by arrow C. This makes it possible to change the orientation of an X-ray output from the X-ray tube.
(2) To adjust the position of the X-ray tube 7 in the lateral direction (Xs), the longitudinal direction (namely, in front and behind directions) (Ys), or the height direction (Zs) in relation to the housing 3, the actuator can cause the X-ray tube 7 to perform a translational movement.

The position in which the X-ray emitted from the X-ray source F is incident on the measurement object 2 can be adjusted by the actions (1) and/or (2) described above. Adjusting the X-ray incident position in this manner makes it possible to maintain the position of the X-ray that is incident on the measurement object 2 in one fixed position even if, for example, the hand that holds the housing 3 is shaking.

An actuator 10B is coupled with the X-ray detector 8. The actuator 10B can perform the following actions:
(1) To adjust the position of the X-ray detector 8, the actuator can cause the X-ray detector to rotatably oscillate around the X-ray radiation point B as shown by arrow D.
(2) To adjust the position of the X-ray detector 8, the actuator can cause the X-ray detector to perform a translational movement toward or away from (the direction of arrow E) the X-ray radiation point B.
(3) To adjust the position of the X-ray detector 8, the actuator can cause the X-ray detector to perform a translational movement in a direction (direction G in the drawing, or a direction at a right angle to direction G) at a right angle to the center line of the X-ray R2 emitted from the measurement object 2.

Actuators 10A and 10B can be configured with a combination of a rotatable oscillation mechanism and a translational mechanism.

Figure 2:
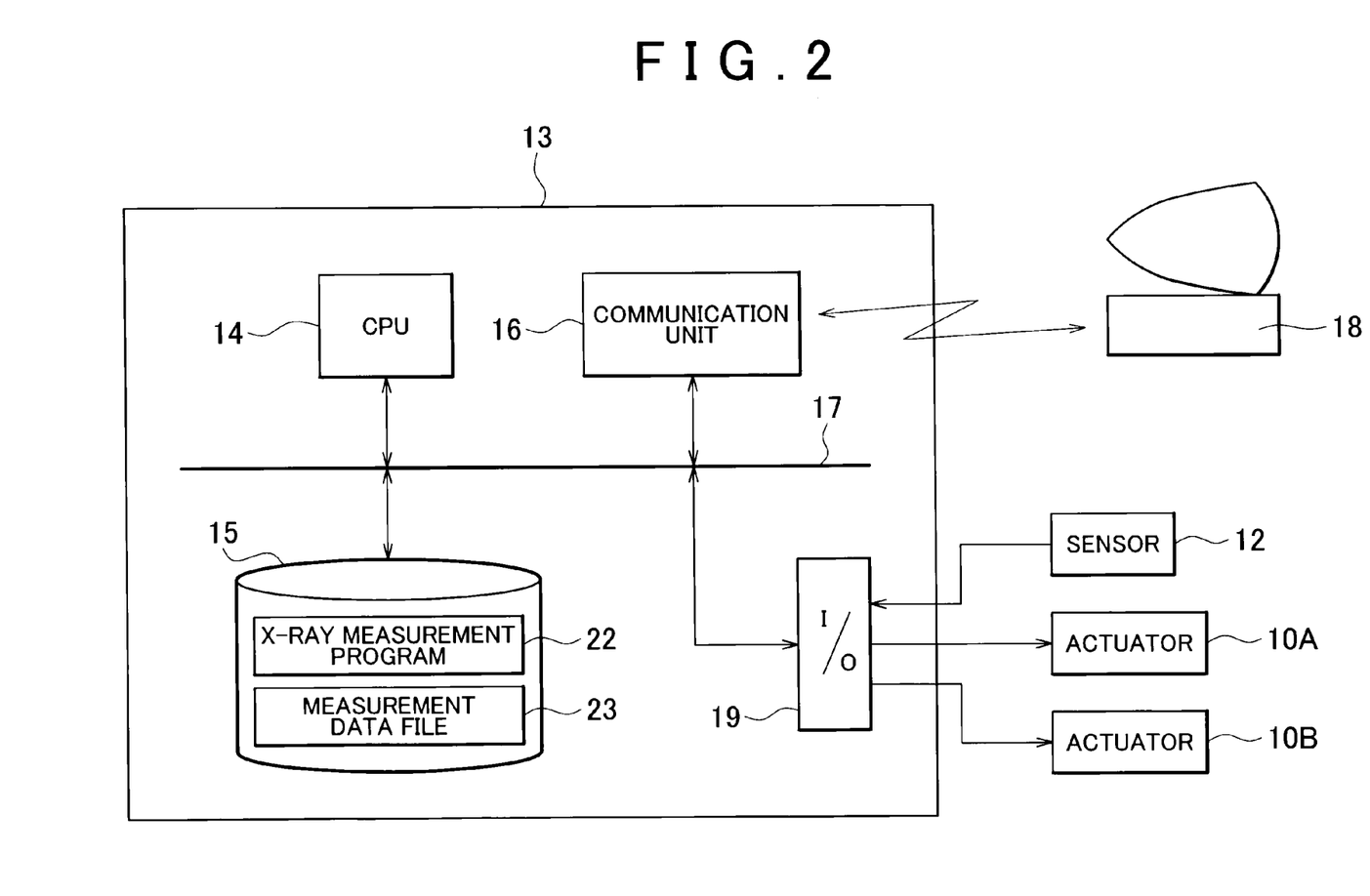
FIG. 2 is a block diagram showing a specific example of a controller that is a principal part of the X-ray measurement apparatus shown in FIG. 1.

The controller 13 has a central processing unit (CPU) 14 which is an arithmetic controller, a memory 15 which is a storage medium, and a communication unit 16, as shown, for example, in FIG. 2. The communication unit 16 communicates data with an external communication instrument 18. The CPU 14, the memory 15, and the communication unit 16 are all linked by a bus 17 which is a data transfer channel. In this embodiment, a personal computer is used as the external communication instrument 18. The distance sensor 12 in FIG. 1 is connected to the CPU 14 via an input-output interface 19 in FIG. 2.

The memory 15 is configured with a mechanical memory such as a hard disk or the like, a semiconductor memory, or any other storage medium. In the storage region of the memory 15 is installed an X-ray measurement program 22 which is a program for realizing X-ray measurement using the various types of instruments shown in FIG. 1. The storage region of the memory 15 also accommodates a measurement data file 23, which is a region for storing measurement result data.

A power source 24 is provided on the exterior of the housing 3 in FIG. 1. Electrical power can be supplied to the various electrical instruments provided inside the housing 3 from the power source 24 via a cable 25. The power source 24 may also be provided inside the housing 3.

When X-ray measurement is performed on the measurement object 2 using the X-ray measurement apparatus in this embodiment, the person performing the measurement first manually grasps the handle 4, brings the entire X-ray measurement apparatus 1 toward the measurement object 2, and positions the aperture 9 in the housing 3 at the desired measurement point on the measurement object 2. The startup switch (not shown) is subsequently set to ON, whereupon the X-ray measurement program 22 shown in FIG. 2 is started up and the function explained below is achieved.

Namely, the X-ray R1 is first emitted from the X-ray tube 7 in FIG. 1. If the angle θi at which the X-ray R1 is incident on the measurement object 2 is made consistent with the angle fulfilling a designated diffraction condition in relation to the crystal lattice surface of the measurement object 2, an X-ray R2 diffracted from the measurement object 2 is generated. The corresponding diffraction angle 2θ of the diffracted X-ray R2 at this time is twice the angle of the incident angle θi. The diffracted x-ray R2 diffracted at the diffraction angle 2θ can be read by the light-receiving surface of the two-dimensional X-ray detector 8 positioned at the angle of view θd in relation to the measurement object 2. The diffracted X-ray is read using the X-ray detector 8 at each designated sampling time (for example, several microseconds (μs)). The angle of view θd of the X-ray detector 8 is an angle equal to the X-ray incident angle θi.

The light-receiving surface of the two-dimensional X-ray detector 8 is a plane having a predetermined surface area, and a position within the plane can be specified with (x, y) coordinates. Therefore, it is possible to specify, with (x, y) coordinates, which pixel (picture element) within the light-receiving surface of the X-ray detector 8 received an X-ray. The X-ray detector 8 transmits the measured X-ray intensity in the form of an electrical signal to the controller 13. The controller 13 prepares diffraction pattern data, which is a two-dimensional diagram, on the basis of the transmitted X-ray intensity data. The diffraction pattern is displayed as an image on the display of the computer 18 in FIG. 2. When the person measuring observes the image, it can be immediately assessed whether there are defects in the measurement object 2.

Figure 3:
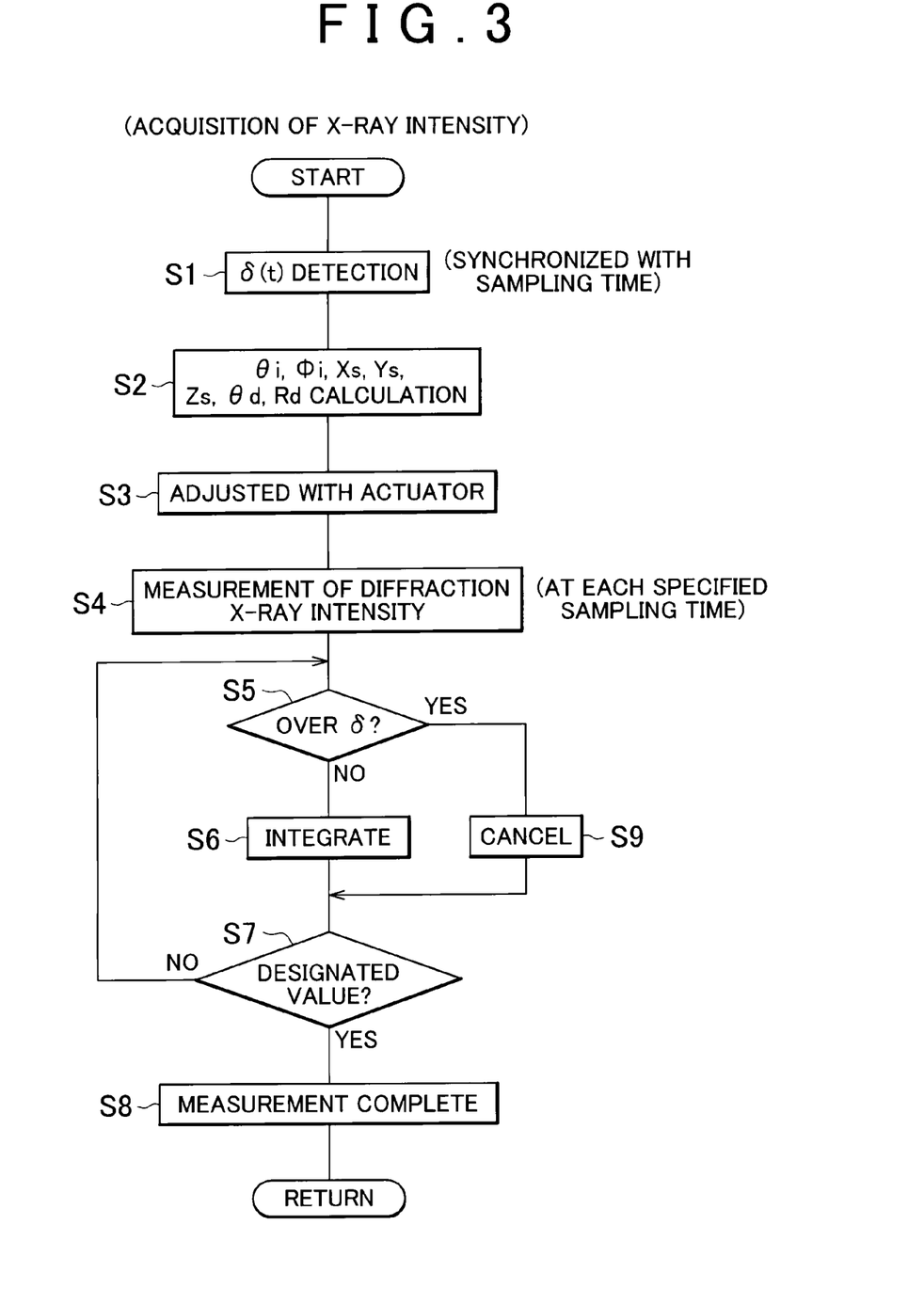
FIG. 3 is a flowchart showing part of the flow of control executed by the controller in FIG. 2.

The X-ray measurement program 22 in the memory 15 in FIG. 2 executes an X-ray measurement operation such as that described above, and this execution process includes a process for obtaining X-ray intensity such as that shown in FIG. 3. Following is an explanation of this process.

First, in step S1, the CPU 14 in FIG. 2 detects the variation quantity δ(t) of the position of the housing 3 in relation to the measurement object 2 using the sensor 12 in FIG. 1 in synchrony with a sampling time of several microseconds (μs), namely, in real time in relation to the X-ray measurement. Here, (t) indicates that the variation quantity is determined at each sampling time.

The variation quantity δ(t) includes variation quantities such as a variation quantity related to the distance (D0) between the vibration quantity detection sensor 12 and the measurement object 2; a variation quantity within a plane orthogonal to the line connecting the vibration quantity detection sensor 12 and the measurement object 2; and a variation quantity related to the inclination of the vibration quantity detection sensor 12 in relation to the measurement object 2.

Next, in step S2, the CPU 14 calculates, on the basis of the variation quantity δ(t) obtained, various measurement condition values for compensating for the variation quantity δ(t). Specifically, the CPU considers the variation quantity δ(t) and calculates the X-ray incident angle δi, the in-plane rotation angle φi, the quantities of translational movement Xs, Ys, and Zs in relation to the X-ray tube 7, the angle of view θd of the X-ray detector 8 in relation to the measurement object 2, and the distance Rd of the X-ray detector 8 from the measurement object 2.

Figure 4:
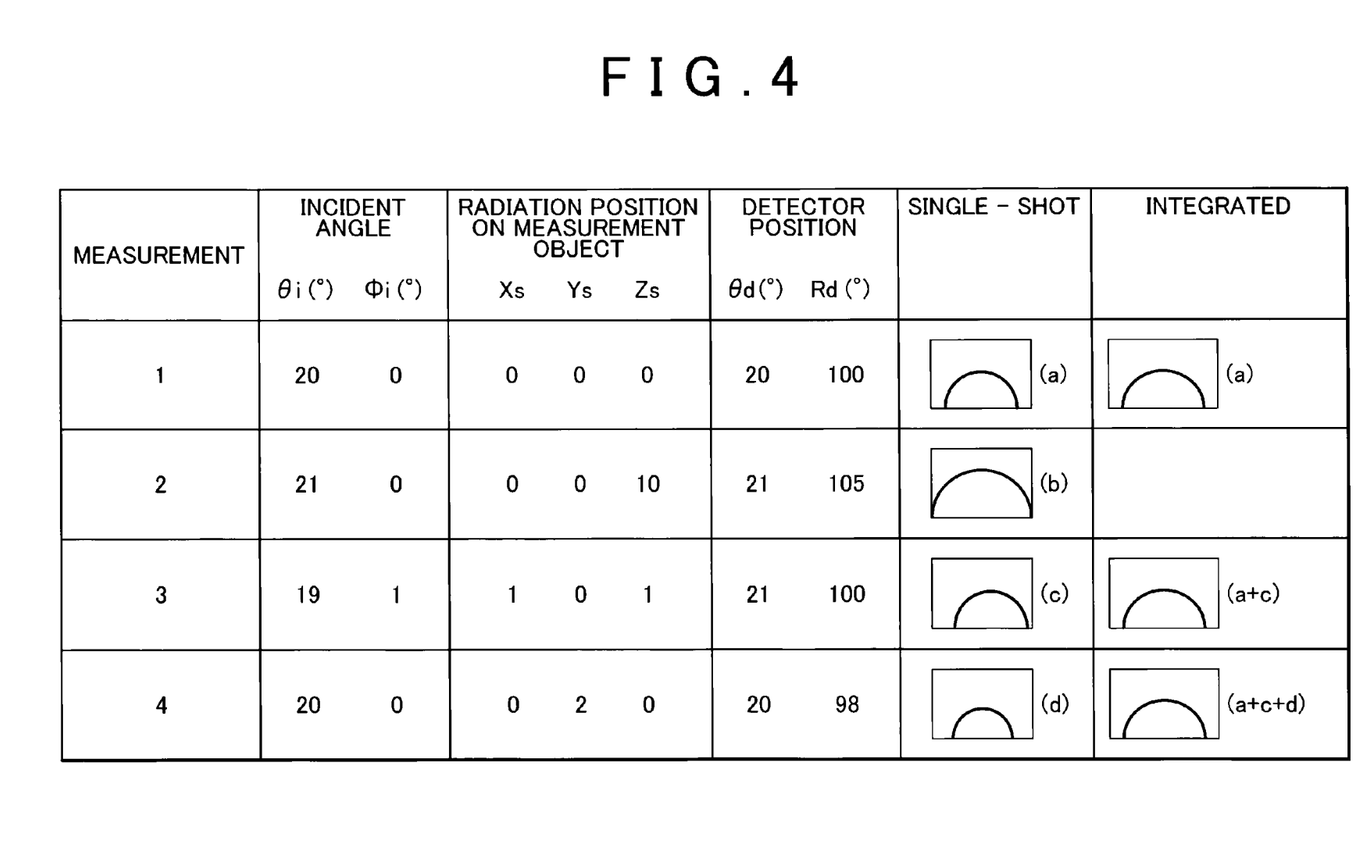
FIG. 4 is a diagram showing part of the content of the control executed by the controller in FIG. 2.

For example, the CPU 14, as shown in FIG. 4, calculates the values θi, φi, Xs, Ys, Zs, θd, and Rd for the four sampling times Nos. 1-4 on the basis of variation quantity δ(t). Next, the CPU 14 operates the actuators 10A and 10B in FIG. 1 on the basis of the resulting condition values to make the values θi, φi, Xs, Ys, Zs, θd, and Rd consistent with the calculation results.

Next the CPU 14 performs X-ray measurement for each of the specified sampling times Nos. 1-4. Specifically, an X-ray is emitted from the X-ray tube 7 in FIG. 1 and radiated toward the X-ray radiation point B on the measurement object 2. When the X-ray diffracted by the measurement object 2 is generated, the diffracted X-ray is detected by the X-ray detector 8. For example, for each sampling time in FIG. 4, diffracted X-rays similar to (a) through (d) shown in the "Single-shot" column are detected. The data on the diffracted X-rays thus detected is the data after compensation for the position variation quantity of the X-ray measurement apparatus 1 caused by vibration, hand-shaking, and the like, and therefore is correct, highly reliable data.

The CPU 14 integrates the measured single-shot data (step S6), and concludes the measurement when the integration value reaches a designated value (steps S6, S7, S8). When measuring as shown in FIG. 4, the condition value Zs=10 in measurement No. 2 has a variation large enough so that compensation is not possible using the actuator 10A, which is the compensation means in this embodiment. Therefore, the measurement value is discarded and cannot be included in the integration (step S9).

In the X-ray measurement apparatus according to this embodiment, the positions of the X-ray tube 7 and the two-dimensional X-ray detector 8 are corrected on the basis of the variation quantity of the housing 3 detected by the vibration quantity detection sensor 12. Therefore, the X-ray measurement apparatus according to this embodiment is capable of obtaining correct, stable, highly reliable measurement data despite the fact that the X-ray measurement apparatus is portable, and is therefore vulnerable to being affected by hand-shaking, vibration, and the like during measurement.

(Second Embodiment)

In the above-mentioned first embodiment, the vibration quantity detection sensor 12 comprises a distance sensor, a speed sensor, an acceleration sensor, and a gyro sensor. Also, the X-ray tube 7 is capable of performing a rotatable oscillation (along the direction C in FIG. 1) and a translational movement (along the directions Xs, Ys, Zs) to be adjusted the position thereof. Further, the two-dimensional X-ray detector 8 is capable of performing a rotatable oscillation (along the direction D in FIG. 1), a translational movement in relation to the measurement object 2 (along the direction of the direction E in FIG. 1), and a translational movement in a direction at a right angle to the center line of an X-ray R2 (i.e., the direction G and the direction at a right angle to direction G in FIG. 1), to thereby be adjusted the position thereof.

In the X-ray measurement apparatus according to the second embodiment, the X-ray tube 7 is secured to the housing 3 so that the incident angle θi of the X-ray is a fixed value, and the two-dimensional X-ray detector 8 is secured to the housing 3 so that the angle of view θd of the X-ray detector 8 is a fixed value. For this reason, the actuators 10A and 10B shown in FIG. 1 are not used in this embodiment.

Furthermore, in this embodiment, the vibration quantity detection sensor 12 is configured only with the distance sensor using laser light. Therefore, the variation quantity detected by the sensor 12 is only the variation quantity of the distance of the housing 3 from the measurement object 2.

The controller 13 does not compensate for the variation quantity of the housing 3 by mechanically moving the X-ray tube 7 and the X-ray detector 8, but rather compensates numerically by calculating measurement data obtained by the two-dimensional X-ray detector 8 according to the function implemented by a designated software application installed in the memory 15 in FIG. 2. Specifically, the variation quantity of the housing 3 is divided into two orthogonal components within the planar coordinates on the X-ray light-receiving surface of the X-ray detector 8, and the position information in the diffraction data obtained by measurement is compensated for with the variation quantity components.

Also in this second embodiment, the measurement information of the two-dimensional X-ray detector 8 is compensated for on the basis of the variation quantity of the housing 3 detected by the vibration quantity detection sensor 12. Therefore, the X-ray measurement apparatus according to this embodiment is capable of obtaining correct, stable, highly reliable measurement data despite the fact that the X-ray measurement apparatus is portable, and is therefore vulnerable to being affected by hand-shaking, vibration, and the like during measurement.

(Example of Modification)

In the above-mentioned second embodiment, the X-ray tube 7 is secured to the housing 3, and the two-dimensional X-ray detector 8 is secured to the housing 3, whereupon the measurement data obtained by the two-dimensional X-ray detector 8 is numerically compensated by calculation according to the function implemented by a software application. A separate configuration can also be adopted in which the position of the X-ray tube 7 can be adjusted with the actuator 10A, and the position of the two-dimensional X-ray detector 8 can be adjusted with the actuator 10B, whereupon the measurement data obtained by the two-dimensional X-ray detector 8 is compensated for numerically by calculation according to a function implemented by the software application.

(Other Embodiments)

Above, the present invention is explained with reference to the preferred embodiments, but the present invention is not limited to these embodiments, and various modifications may be possible within the scope of the invention described in the claims.

For example, in the above-mentioned first embodiment, the vibration quantity detection sensor 12 in FIG. 1 is configured with sensors such as a distance sensor, a speed sensor, an acceleration sensor, and a gyro sensor. Also, in order to adjust the position of the X-ray tube 7, rotatable oscillation (direction C in FIG. 1) and translational movement (Xs, Ys, Zs) are enabled. Also, in order to adjust the position of the two-dimensional X-ray detector 8, the X-ray detector is made capable of rotatable oscillation (direction D in FIG. 1), translational movement (direction E in FIG. 1) in relation to a measurement object 2, and translational movement in a direction (direction G in FIG. 1, or a direction at a right angle to direction G) at a right angle to the center line of an X-ray R2.

However, the vibration quantity detection sensor 12 is not limited to cases in which the sensor is configured including all of the distance sensor, speed sensor, acceleration sensor, and gyro sensor, but can be one or a combination of two or three of the distance sensor, speed sensor, acceleration sensor, and gyro sensor. Also, any sensors other than the distance sensor, speed sensor, acceleration sensor, and gyro sensor may be used.

Also, the present invention is not limited to cases in which both the X-ray tube 7 and the two-dimensional X-ray detector 8 are moved for positional adjustment, but a configuration is also possible in which either may be moved selectively for positional adjustment.

In the embodiments explained above, the direction of advance of the incident X-ray R1 is adjusted by mechanically moving the X-ray tube 7 with the actuator 10A. However, an electrode can also be provided on the interior or the exterior of the X-ray tube 7, and the direction of advance of the incident X-ray R1 can be adjusted by the action of a magnetic field formed by the electrode.

(Explanation of Symbols)

1: X-ray measurement apparatus, 2: Measurement object, 3: Housing (container), 4: Handle, 7: X-ray tube (X-ray generator), 8: Two-dimensional X-ray detector (X-ray-detection means), 9: Aperture, 10A, 10B: Actuator (the compensation means), 12: Vibration quantity detection sensor, 13: Controller, 14: CPU, 15: Memory, 16: Communication unit, 17: Bus, 18: Computer (external communication instrument), 19: Input-output interface, 25: Cable, B: X-ray-radiation point, C,D: Direction of rotatable oscillation, E: Direction of translational movement, F: X-ray focus (X-ray source), L0: Length, H0: Height, R1: Incident X-ray, R2: Diffracted X-ray, X0: Center line in height direction, $f_i$: Incident angle, $\theta_d$: Angle of view of X-ray detector, $2\theta$: Diffraction angle, $\phi_i$: In-plane angle

What is claimed is:

1. An X-ray measurement apparatus having:
    an X-ray source for generating an X-ray incident on a measurement object;
    X-ray detection means for detecting an X-ray leaving the measurement object; and
    a housing containing the X-ray source and the X-ray detection means;
    the X-ray measurement apparatus comprising:
    a vibration quantity detection sensor for detecting a vibration quantity of the housing; and
    a controller for controlling the X-ray source, the X-ray detection means and the vibration quantity detection sensor, wherein the controller:
        obtains X-ray intensity at each sampling time by using the X-ray detection means;
        integrates the obtained X-ray intensity;
        detects the vibration quantity at each sampling time by using the vibration quantity detection sensor;
        determines a variation quantity of a position of the housing in relation to the measurement object based on the vibration quantity;
        determines measurement condition values based on the variation quantity for compensation for the variation quantity; and
        when any one of the measurement condition values has a variation large enough so that compensation is not possible, the corresponding X-ray intensity is not included in the integration.

2. The X-ray measurement apparatus according to claim 1, wherein the vibration quantity detected by the vibration quantity detection sensor is at least one of:
    (A) the amount of variation in distance between the vibration quantity detection sensor and the measurement object;
    (B) the amount of variation within a plane orthogonal to a line connecting the vibration quantity detection sensor and the measurement object; or
    (C) the amount of variation in inclination of the vibration quantity detection sensor relative to the measurement object.

3. The X-ray measurement apparatus according to claim 2, wherein the vibration quantity detection sensor comprises any one or a combination of two or more of a distance sensor for detecting variation in distance, a speed sensor for detecting variation in speed, an acceleration sensor for detecting variation in acceleration, and an angular velocity sensor for detecting variation in angular velocity of the X-ray measurement apparatus.

4. The X-ray measurement apparatus according to claim 1, wherein the vibration quantity detection sensor is secured to the housing.

5. The X-ray measurement apparatus according to claim 1, wherein the process for correcting a measurement value obtained using the X-ray detection means is performed by controlling the position of the X-ray detection means.

6. The X-ray measurement apparatus according to claim 5, wherein controlling the position of the X-ray detection means causes variation in the distance between the X-ray detection means and the measurement object.

7. The X-ray measurement apparatus according to claim 5, wherein controlling the position of the X-ray detection means causes movement of the X-ray detection means in a direction at a right angle to the center line of the X-ray leaving the measurement object.

8. The X-ray measurement apparatus according to claim 5, wherein controlling the position of the X-ray detection means causes variation in the inclination angle of the X-ray detection means in relation to the measurement object.

9. The X-ray measurement apparatus according to claim 5, wherein controlling the position of the X-ray detection means is a combination of any two or three of the following:
    causing variation in the distance between the X-ray detection means and the measurement object;
    causing movement of the X-ray detection means in a direction at a right angle to the center line of an X-ray leaving the measurement object; and
    causing variation in the inclination angle of the X-ray detection means in relation to the measurement object.

10. The X-ray measurement apparatus according to claim 1, wherein the process for correcting a measurement value obtained using the X-ray detection means is a process for causing the X-ray that leaves the X-ray source and is incident on the measurement object to be incident on the measurement object at a fixed position.

11. The X-ray measurement apparatus according to claim 10, wherein the process for causing the X-ray that leaves the X-ray source and is incident on the measurement object to be incident on the measurement object at a fixed position controls the orientation of the X-ray source in relation to the measurement object.

12. The X-ray measurement apparatus according to claim 10, wherein the process for causing the X-ray that leaves the X-ray source and is incident on the measurement object to be incident on the measurement object at a fixed position controls the direction of advance of the X-ray leaving the X-ray source by controlling the position of at least one of a plurality of X-ray optical elements constituting an incident optical system, the X-ray optical elements including the X-ray source.

13. The X-ray measurement apparatus according to claim 1, wherein the process for correcting a measurement value obtained using the X-ray detection means is a process in which the data obtained by the X-ray detection means is calculated by a software program.

14. The X-ray measurement apparatus according to claim 1, wherein the X-ray detection means is a one-dimensional X-ray detector, a two-dimensional X-ray detector, or a pixel detector.

15. The X-ray measurement apparatus according to claim 1, wherein the housing can be carried manually by a person, and the person performs measurement while manually holding the housing and placing an opening in the housing for outputting an X-ray so that the opening faces the measurement object.

16. The X-ray measurement apparatus according to claim 3, wherein the vibration quantity detection sensor is secured to the housing.

17. The X-ray measurement apparatus according to claim 16, wherein the process for correcting a measurement value obtained using the X-ray detection means is performed by controlling the position of the X-ray detection means.

18. The X-ray measurement apparatus according to claim 16, wherein the process for correcting a measurement value obtained using the X-ray detection means is a process for causing the X-ray that leaves the X-ray source and is incident on the measurement object to be incident on the measurement object at a fixed position.

19. The X-ray measurement apparatus according to claim 16, wherein the process for correcting a measurement value obtained using the X-ray detection means is a process in which the data obtained by the X-ray detection means is calculated by a software program.

\* \* \* \* \*